(12) United States Patent
Castellini

(10) Patent No.: US 6,991,458 B2
(45) Date of Patent: Jan. 31, 2006

(54) METHOD FOR STERILIZING THE WATER CIRCUITS OF DENTAL APPARATUS AND APPARATUS IMPLEMENTING THE METHOD

(75) Inventor: Franco Castellini, Bologna (IT)

(73) Assignee: Castellini S.p.A., Bologna (IT)

( * ) Notice: Subject to any disclaimer, the term of this patent is extended or adjusted under 35 U.S.C. 154(b) by 1 day.

(21) Appl. No.: 10/396,661

(22) Filed: Mar. 25, 2003

(65) Prior Publication Data

US 2004/0191721 A1 Sep. 30, 2004

(51) Int. Cl.
 *A61C 17/02* (2006.01)
(52) U.S. Cl. ...................................................... 433/80
(58) Field of Classification Search ............... 422/28, 422/1; 433/82, 80, 84
 See application file for complete search history.

(56) References Cited

U.S. PATENT DOCUMENTS

| 4,545,956 | A |   | 10/1985 | Ciszewski et al. |
|---|---|---|---|---|
| 5,087,198 | A | * | 2/1992 | Castellini ............... 433/80 |
| 5,709,546 | A |   | 1/1998 | Waggoner |
| 5,785,523 | A |   | 7/1998 | Overmyer |
| 6,250,920 | B1 | * | 6/2001 | Overmyer ............... 433/80 |

FOREIGN PATENT DOCUMENTS

| EP | 0 317 521 B2 |   | 10/1988 |
|---|---|---|---|
| EP | 403442 A2 | * | 12/1990 |
| EP | 0 111 249 B2 |   | 2/1995 |
| EP | 1 161 959 A1 |   | 12/2001 |

OTHER PUBLICATIONS

European Search Report corresponding to EP Application Number EP 02 02 8933.

* cited by examiner

*Primary Examiner*—Melba N. Bumgarner
(74) *Attorney, Agent, or Firm*—Fay, Sharpe, Fagan, Minnich & McKee, LLP

(57) ABSTRACT

The invention relates to a method for sterilizing/disinfecting water circuits of dental units (1) comprising dental handpieces (2) and a water circuit (3) for supplying liquid from a main supply (4) through corresponding circuit legs or branches (3a, 3b, 3c, 3s). The method comprises at least the following steps: introducing a disinfectant/sterilizing liquid in the water circuit (3) for a predetermined length of time; draining the disinfectant/sterilizing liquid out of the circuit (3) through the circuit legs or branches (3a, 3b, 3c, 3s); and introducing the user liquid in the water circuit (3); the method further comprising, between the steps of introducing and draining out the disinfectant/sterilizing liquid and the user liquid, a step of introducing a fluid from an independent branch (5) in the water circuit (3) for a predetermined length of time, depending on defined parameters, in order to expel from the water circuit (3) all the remaining liquid in the water circuit (3).

7 Claims, 1 Drawing Sheet

METHOD FOR STERILIZING THE WATER CIRCUITS OF DENTAL APPARATUS AND APPARATUS IMPLEMENTING THE METHOD

BACKGROUND OF THE INVENTION

The present invention relates to a method for sterilizing the water circuits of dental apparatus and to the dental apparatus implementing the method.

In the manufacturing of dental equipment, one of the fundamental parts, if not the "heart", of a dental unit is its water and air circuit, where the water line supplies fluids used by dental equipment and patients (water or physiological saline for tumblers and handpieces), or consumer units (swilling water for the spittoon), while the air line is used for certain items of equipment (air spray handpieces, cooling air and driving air).

With increases in general standards of hygiene and with dental apparatus and equipment becoming more and more "fragile", several design solutions have been found for the water and air circuits of dental units, not only to guarantee their efficient operation and durability but also to maintain the sterility of the conduits during patient treatments. Considering that the basic structure of these fluid circuits comprises a first main line supplying water from the mains, and a second main line supplying air from an external source (compressor), each of which has a plurality of branches leading to the operating and accessory equipment of the dental unit, different systems have been designed on the basis of different methods aimed at improving the functioning and disinfection of these fluid lines or parts of them.

In particular, the present specification focuses attention on the water line which is disinfected according to two different methods, one with a continuous cycle and the other with a discontinuous cycle, and both requiring additional devices to be fitted to the basic structure of the circuit.

The present specification is concerned in particular with the solutions based on the discontinuous disinfection/sterilization cycle. In this type of cycle, as disclosed in patent publications EP-111.249 and EP-317.521 (the latter being by the present Applicant), the mains water supply is shut off, and a dedicated branch equipped with an independent tank is used to feed sterilizing liquid into the conduits that supply water to the handpieces.

After a preset time, depending on the quality of disinfection/sterilization required and the properties of the sterilizing liquid, the line is opened again and the sterilizing liquid drained out.

The drainage of the sterilizing liquid is performed by flushing water (or a user fluid) supplied by the main line (or by a dedicated line) and opening the control valves on the handpieces so that the water or user fluid expels the sterilizing liquid, rinses the water line and flows out into an appropriate drain.

Although this method, which has been used on dental units for some time, has proved to be very effective and practical, the Applicant, in line with a policy of continual improvement of dental unit sanitizing procedures, has continued conducting research and development targeted to improving safety by adding innovative elements and features to sterilizing procedures in order to enhance the performance of the sanitizing products used and, consequently, to increase the safety of the dental equipment.

The aim of the present invention is therefore to provide a dental apparatus sterilizing/disinfecting method that is safe and practical, enhances the performance of the products used and at the same time reduces down time during changes of fluids.

SUMMARY OF THE INVENTION

The above mentioned aim is achieved in a method for sterilizing/disinfecting water circuits of dental units comprising dental handpieces and a water circuit for supplying a liquid from a main supply through corresponding circuit legs or branches, the method comprising at least the following steps: introducing a disinfectant/sterilizing liquid in the water circuit for a predetermined length of time; draining the disinfectant/sterilizing liquid out of the circuit through the circuit legs or branches; and introducing the user liquid in the water circuit; the method further comprising, between the steps of introducing and draining out the disinfectant/sterilizing liquid and the user liquid, a step of introducing a fluid from an independent branch in the water circuit for a predetermined length of time depending on defined parameters in order to expel from the water circuit all the remaining liquid in the water circuit.

BRIEF DESCRIPTION OF THE DRAWINGS

The technical characteristics of the invention, with reference to the above aims, are clearly described in the claims below and its advantages are apparent from the detailed description which follows, with reference to the accompanying FIG. 1 which is a diagram representing the water circuit of a dental unit implementing the method according to the present invention.

DESCRIPTION OF THE PREFERRED EMBODIMENTS

Figure 1:
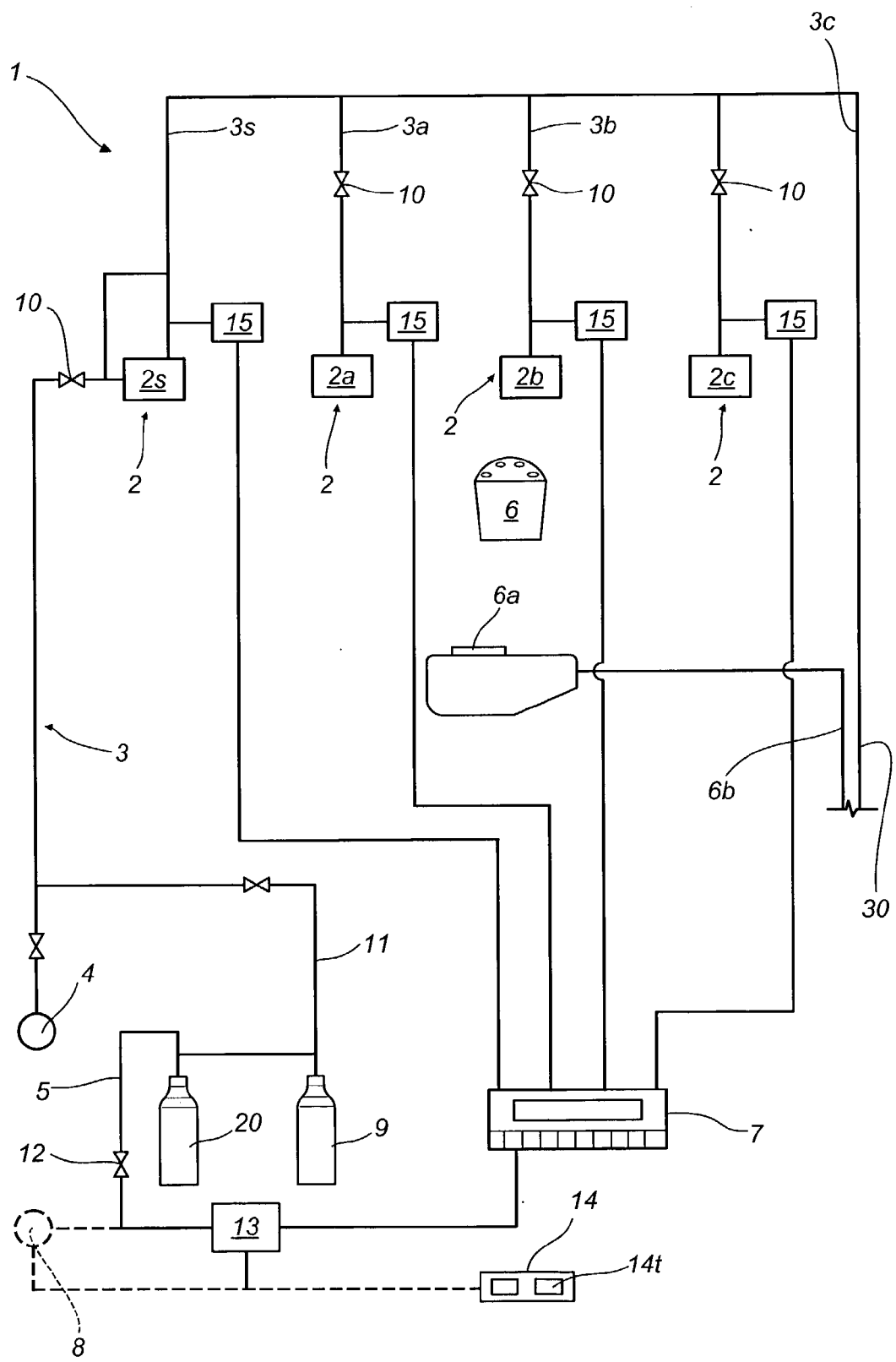

With reference to the accompanying drawing, the method according to the invention is used to sterilize/disinfect the water circuits of dental apparatus.

More specifically, this apparatus is embodied in a dental unit 1 of the type comprising, at least insofar as is relevant to the present invention, medical instruments 2 such as dental handpieces (for example, a micromotor 2a, a turbine 2b, an ablator 2c and a syringe 2s) and similar equipment; in addition to these, the dental unit comprises a water circuit 3 that supplies a liquid that may come from a mains supply 4 and a drain 30 for the liquid itself.

The water circuit 3 is divided into a plurality of branches 3s, 3a, 3b, 3c, each leading to one of the handpieces 2 present on the dental unit 1 and necessitating a fluid supply.

The dental unit 1 can therefore be used to implement a method comprising the steps of:

introducing a disinfectant/sterilizing liquid in the water circuit 3 for a predetermined length of time;

draining the disinfectant/sterilizing liquid out of the circuit 3 through the circuit legs or branches 3a, 3b, 3c, 3s;

introducing a user liquid into the water circuit 3.

In addition to these basic steps, the method further comprises, between the steps of introducing and draining out the disinfectant/sterilizing liquid and the user liquid, a step of introducing another fluid from an independent branch 5 in the water circuit 3 for a predetermined length of time, depending on defined parameters, in order to expel from the water circuit 3 all the liquid previously in the water circuit 3.

In particular, the step of introducing this fluid is performed at least once before the step of introducing the disinfectant/sterilizing liquid so that all the user liquid is expelled from the water circuit 3.

Preferably, the step of introducing this fluid is also performed after the step of introducing the disinfectant/sterilizing liquid so that all the disinfectant/sterilizing liquid is expelled from the water circuit 3.

In practice, the full sterilization/disinfection method according to the invention comprises the following steps:

removing at least the end portions of the circuit legs or branches 3a, 3b, 3c, 3s from their respective rest positions and placing them in a container 6 for collecting liquid, such as, for example, a spittoon 6a already present on the dental unit, and having an independent drain 6b;

introducing the fluid in the water circuit 3 so as to completely expel the user liquid from the water circuit 3 and its branches 3a, 3b, 3c, 3s;

introducing a disinfectant/sterilizing liquid in the water circuit 3 and in its branches 3a, 3b, 3c, 3s for a predetermined length of time;

draining the disinfectant/sterilizing liquid out of the water circuit 3 through the circuit legs or branches 3a, 3b, 3c, 3s;

introducing the fluid again so as to completely expel the disinfectant/sterilizing liquid from the water circuit 3 and its branches 3a, 3b, 3c, 3s;

introducing the user liquid in the water circuit 3 and in its legs or branches 3a, 3b, 3c, 3s;

Obviously, and as is well within the knowledge of experts in the trade familiar with methods of this kind, shutoff means are opened and closed during these steps in order to allow the liquids and the fluid to flow into the water circuit 3, be held there and then drained out.

Preferably, but without restricting the scope of the invention, the dental unit 1 may be equipped with a microprocessor unit 7 that controls the main and auxiliary functions of the dental unit 1. When this is the case, the steps of introducing the fluid are controlled by the microprocessor unit 7 and can be programmed according to the above mentioned parameters, that is to say, are predetermined to last for a length of time at least sufficient to completely expel the liquid present (either disinfectant/sterilizing liquid or user liquid) from the water circuit 3 or its legs or branches 3a, 3b, 3c, 3s.

For example, the fluid introduced in the first case may be air under pressure from an independent circuit 8.

On the other hand, the user liquids may, as is well known, be water from the mains water supply 4, or a sterile liquid, or physiological saline from an independent container 9 connected to the water circuit 3.

The dental unit 1 that implements the method described above comprises: the aforementioned main water circuit 3 for supplying a liquid to each handpiece 2 present on the dental unit 1, each handpiece 2 being equipped with first shutoff means 10, consisting, for example, of shutoff valves, for turning off the liquid supply; a first independent circuit branch 11 which, when required, introduces in the water circuit 3 the disinfectant/sterilizing liquid from a container 20; and an air circuit 13 (only partly shown in the accompanying drawing, since it is of well-known type) which is used for driving and auxiliary functions of the handpieces 2 and of accessory equipment present on the dental unit 1.

As already mentioned, the dental unit 1 is equipped with a microprocessor unit 7 that controls its main and auxiliary functions.

As illustrated in FIG. 1, the dental unit comprises an additional circuit branch 5, which supplies a gaseous fluid and which is connected to the water circuit 3 upstream of the handpieces 2, so that, when required, all the liquid present in the water circuit 3 can be expelled from the water circuit 3.

More specifically, the additional circuit branch 5 is connected to the first independent circuit branch 11 so that fluid can be introduced in all parts of the water circuit 3 and can empty the water circuit 3 completely.

The additional supply branch 5 may be equipped with second shutoff means 12—for example, a valve—designed to allow the gaseous fluid to flow into the water circuit 3 when required.

The gaseous fluid supplied by the additional circuit branch 5 may be connected to a self-contained unit 8 (for example, a compressor) for generating the gaseous fluid. Alternatively, the additional branch 5 may be connected directly to the aforementioned air circuit 13 of the dental unit 1, thus using an existing source of compressed air.

The second shutoff means 12 of the additional branch 5 may be controlled by manual control elements 14 mounted on the dental unit 1, such as customary pushbuttons, with or without a timing element 14t, and designed to switch the flow of gaseous fluid to the water circuit 3 on and off for the predetermined length of time required to empty the water circuit 3 itself.

Alternatively, the second shutoff means 12 may be controlled (as mentioned above) by the microprocessor unit 7, which may be programmed with specified time periods for introducing the gaseous fluid in accordance with predetermined parameters, that is to say, a length of time at least sufficient to expel all the liquid from the water circuit 3.

Another possible accessory feature of the dental unit 1 is constituted by sensor means 15 mounted in the water circuit 3 and designed to detect the presence of liquid draining out of the water circuit 3 itself.

These sensor means 15, represented as a series of blocks in the accompanying drawing, may be mounted at the downstream end of the water circuit 3, that is to say, at the ends of the circuit legs or branches 3a, 3b, 3c, 3s connected to the handpieces 2 of the dental unit 1. The sensors 15 may be connected directly to the microprocessor unit 7 so that the flow of gaseous fluid can be stopped immediately as soon as the water circuit is completely empty.

The method and dental unit as described above therefore achieve the preset aim thanks to a simple yet effective step of emptying the water circuit quickly and easily using air: this not only improves the effectiveness of the sterilization/disinfection cycle by preventing the disinfectant/sterilizing liquid from being diluted by another liquid already present in the water circuit, but also speeds up the cycle by direct interaction with it and through a simple dental unit structure, since air can be introduced in the water circuit by simply connecting the air circuit of the dental unit to the water circuit of the dental unit.

The invention described can be subject to modifications and variations without thereby departing from the scope of the inventive concept. Moreover, all the details of the invention may be substituted by technically equivalent elements.

What is claimed is:

1. A method for sterilizing or disinfecting water circuits of dental apparatus for supplying user liquid to handpieces comprising at least the following steps: introducing a disinfectant or sterilizing liquid in a water circuit for a predetermined length of time; draining the disinfectant or sterilizing liquid out of the water circuit introducing a user liquid in the water circuit; introducing air under pressure from an independent branch into the water circuit for a predetermined length of time, depending on defined parameters, in order to expel from the water circuit all the liquid present therein and detecting the presence of liquid draining out of the water circuit; the step of introducing air under pressure and the step of detecting the presence of liquid draining out of the water circuit being controlled by a microprocessor unit for stopping immediately the introduction of air under pressure as soon as the water circuit is completely empty of liquid.

2. The method according to claim 1, wherein the step of introducing air under pressure into the water circuit precedes the step of introducing the disinfectant or sterilizing liquid so that all liquid inside the water circuit is expelled from the water circuit.

3. The method according to claim 1, wherein the step of introducing air under pressure in the water circuit follows the step of introducing the disinfectant or sterilizing liquid so that all the disinfectant or sterilizing liquid is expelled from the water circuit.

4. The method according to claim 1, wherein the user liquid is water from a main water supply.

5. The method according to claim 1, wherein the user liquid is a sterile liquid from an independent container connected to the water circuit.

6. The method according to claim 1, wherein the user liquid is physiological saline from an independent container connected to the water circuit.

7. Method for sterilizing water circuit of dental apparatus for supplying user liquid to handpieces comprising the step of removing at least end portions of circuit legs or branches of the water circuit from their respective rest positions and placing them in a container for collecting liquid; introducing air under pressure in the water circuit; detecting the presence of liquid draining out of the water circuit and stopping immediately the introduction of air under pressure as soon as the water circuit is completely empty from liquid so as to completely expel the user liquid from the water circuit; introducing a sterilizing liquid in the water circuit for a predetermined length of time; draining the sterilizing liquid out of the water circuit; introducing air under pressure again; detecting the presence of liquid draining out of the water circuit and stopping immediately the introduction of air under pressure as soon as the water circuit is completely empty from liquid so as to completely expel the sterilizing liquid from the water circuit and introducing the user liquid in the water circuit.

* * * * *